United States Patent [19]

Ishii et al.

[11] Patent Number: 4,563,462

[45] Date of Patent: Jan. 7, 1986

[54] SUBSTANCE AX-2, A PROCESS FOR PRODUCING THE SAME AND AN ANTITUMOR COMPOSITION CONTAINING THE SAME

[75] Inventors: Shinzo Ishii; Shigeo Katsumata; Yuko Arai; Tadashi Ashizawa; Makoto Morimoto, all of Shizuoka; Kunikatsu Shirahata, Tokyo; Yutaka Saito, Tokyo; Motomichi Kono, Tokyo, all of Japan

[73] Assignee: Kyowa Hakko Kogyo Kabushiki, Tokyo, Japan

[21] Appl. No.: 546,142

[22] Filed: Oct. 27, 1983

[30] Foreign Application Priority Data

Oct. 28, 1982 [JP] Japan .................................. 57-189467

[51] Int. Cl.[4] ..................... C12P 17/18; C07D 471/16; A61K 31/47
[52] U.S. Cl. ....................................... 514/288; 546/66; 435/119
[58] Field of Search ........................... 546/66; 514/288

[56] References Cited

FOREIGN PATENT DOCUMENTS 34-7597 8/1959 Japan .

OTHER PUBLICATIONS

Hamana, Chem. Abstracts, vol. 96, (1982), Entry 85538m.

Saeki et al., Chem. Abstracts, vol. 93, (1980), Entry 186210s.

Ueda et al., Chem. Abstracts, vol. 100, (1984), Entry 28302g.

*Primary Examiner*—Donald G. Daus
*Assistant Examiner*—William A. Teoli, Jr.
*Attorney, Agent, or Firm*—Wolder, Gross & Yavner

[57] ABSTRACT

A substance designated by us as AX-2 and represented by the formula:

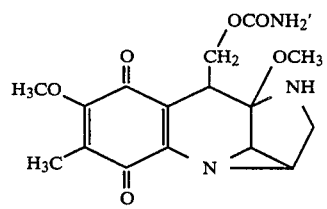

This substance is produced by culturing a microorganism of the genus Streptomyces and capable of producing AX-2 in a medium to accumulate AX-2 in the cultured broth and isolating AX-2 therefrom.

An anti-tumor composition comprising an effective amount of AX-2 in association with a physiologically acceptable carrier or excipient, which is active against Sarcoma 180.

4 Claims, No Drawings

SUBSTANCE AX-2, A PROCESS FOR PRODUCING THE SAME AND AN ANTITUMOR COMPOSITION CONTAINING THE SAME

BACKGROUND OF THE INVENTION

This invention relates to a new substance having anti-tumour activity, a process for producing the same by fermentation and an antitumour composition containing the same.

It was previously known to produce mitomycin A and/or B by fermentation, which process comprises culturing a microorganism of *Streptomyces caespitosus* or mutant strain thereof in a medium to accumulate mitomycin A and/or B in the cultured liquor and recovering mitomycin A and/or B therefrom. In this case, the filtrate of the cultured liquor is treated by using active carbon to adsorb the active substances which are then extracted with a solvent such as acetone, pyridine and the like. The extracted solution is concentrated and the active substances are extracted from the concentrated solution with various organic solvents. Alternatively, the cultured liquor is treated with various organic solvents and the solution containing the active substances is added with anhydrous sodium sulfate and concentrated. It is also possible to adsorb the active substances with active alumina and extracted with various organic solvents.

The present invention is based upon the discovery that a new substance having anti-tumour activity, designated by us as AX-2, may be obtained by treating the filtrate of the cultured broth of a strain of *Streptomyces caespitosus*.

SUMMARY OF THE INVENTION

The present invention is directed to provide a new substance AX-2 having an anti-tumour activity, a process for producing the same by fermentation and an anti-tumour composition containing the same as active ingredient.

According to one feature of the present invention, there is provided a substance AX-2 represented by the following formula:

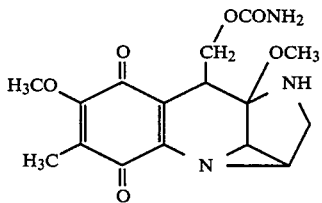

Substance AX-2 has the following physico-chemical characteristics:

(1) Melting point: 75.5°–77.5° C.

(2) Elemental analysis: Found (%) C 55.16, H 5.55, N 11.74.

(3) Specific rotation: $[\alpha]_D = -27.3°$ (c=0.17 CHCl$_3$)

(4) Mass spectrum: m/z M+349 288 98

(5) Ultraviolet absorption spectrum: in methanol: $\lambda_{max}$205 nm ($\epsilon$10800), 294 nm ($\epsilon$5200)

(6) $^1$H-NMH spectrum: $\delta$(CDCl$_3$):
1.84 (1H, br), 1.94 (3H, s), 2.84 (1H,d), 3.14 (1H, t), 3.17 (1H, d), 3.33 (1H, dd), 3.38 (3H, s), 3.57 (1H, dd), 4.03 (3H, s), 4.29 (1H, dd), 4.44 (1H, dd), 4.72 (2H, br, s)

(7) $^{13}$C-NMR spectrum: $\delta$(CDCl$_3$):
8.4, 40.6, 42.9, 46.8, 49.1, 51.0, 61.0, 63.1, 92.4, 126.7, 128.4, 148.6, 156.4, 156.8, 181.1, 184.6

(8) Infrared absorption spectrum: KBr tablet method: 3350, 1710, 1641, 1591, 1076 cm$^{-1}$.

(9) Thin layer chromatography:

| Substance AX-2 | chloroform/methanol = 9:1 (v/v) | toluene/acetone = 35:65 (v/v) | ethyl acetate/acetone = 3:2 (v/v) |
|---|---|---|---|
| Rf value | 0.51 | 0.79 | 0.82 |

(10) Solubility:

Soluble in ethyl acetate, chloroform, acetone, methanol and ethanol. Slightly soluble in water. Insoluble in petroleum ether and n-hexane.

According to another feature of the present invention, there is provided a process for producing substance AX-2 as hereinbefore defined, which comprises culturing a microorganism of the genus *Streptomyces* and capable of producing substance AX-2 in a medium to accumulate AX-2 in the cultured broth and isolating AX-2 therefrom.

Any and all strains belonging to the genus Streptomyces and capable of producing AX-2 by fermentation may be used for the process of the present invention. A preferred strain used in the example described hereinafter is *Streptomyces caespitosus* T-17-135 (NRRL 12508). The mycological characteristics of this strain are disclosed in Japanese Patent Publication No. 7597/59. The mutant strains of this microorganism may also be used for the process of the present invention in so far as they are capable of producing AX-2 by fermentation.

For culturing the microorganisms, both synthetic and organic media containing suitable amounts of carbon sources, nitrogen sources, inorganic substances, and if desired, other nutrients. Suitable carbon sources are exemplified by glucose, glycerol, fructose, maltose, mannitol, xylose, galactose, lactose, ribose, dextrin, starch and starch hydrolyzate and other carbohydrates which may be used solely or in combination. Suitable nitrogen sources are exemplified by ammonia, ammonium chloride, ammonium phosphate, ammonium nitrate, ammonium sulfate, ammonium acetate and other inorganic and organic ammonium salts; urea, peptone, NZ-amine, meat extract, dried yeast, yeast extract, corn steep liquor, casein hydrolyzate, fish meal and digested products thereof, soybean meal and digested products thereof; glycine, glutamic acid, alanine and other amino acids etc. As inorganic substances, for example, phsophates, sodium chloride, calcium carbonate and small amounts of heavy metallic salts may be used, although the addition of such inorganic substances may, if desired, be omitted in the case of using media containing naturally occuring substances. Where mutant strains requiring nutrients are used, it is necessary to add the required nutrients to the media.

Aerobic culturing such as, for example, culturing with shaking, steep culturing with shaking and aeration and the like may be preferred for culturing the strain, which may usually be effected at a temperature of from 25° to 35° C. for 3 to 4 days to accumulate AX-2 in the cultured broth, from which AX-2 may be recovered, for example, in the following manner.

After completion of the culturing, for example, propanol is added to the cultured broth to prevent the decomposition of the active substance. A suitable filter aid such as, for example, Radiolite #600 (commercial product of Showa Kagaku Kogyo K.K., Japan) is added to the mixture which is then filtered to remove the cells. The filtrate is passed through a suitable resin such as, for example, Diaion HP-20 (a synthetic resin commercially avilable from Mitsubishi Kasei Kogyo K.K., Tokyo) to adsorb mitomycin A, B and AX-2 onto the resin, from which a major portion of mitomycin B is eluted with 30-60% methanol. Then 60-100% methanol is applied to the resin to elute AX-2, mitomycin A and a very small amount of mitomycin B. The effluent is then concentrated in vacuo and extracted by using ethyl acetate. The extracted active substance is present in the solvent layer, which is then concentrated in vacuo and petroleum ether is added to the concentrated solution to form a precipitate, from which crude AX-2 is obtained in the from of powder. The crude powder is subjected to silica gel chromatography using a solvent system of chloroform/methanol (100:3 v/v) to give fractions containing AX-2 which are collected, combined and concentrated in vacuo. To the concentrated fraction is added petroleum ether to form a precipitate of AX-2 in the form of yellowish brown powder.

Alternatively, the synthetic resin (Diaion HP-20) is washed with water and extracted, for example, with an aqueous acetone (e.g. 15%) to remove impurities, followed by further extraction with acetone (e.g. 40%) to obtain a fraction containing AX-2 which is then concentrated in vacuo. Sodium chloride solution is added to the concentrated solution at a concentration of sodium chloride of e.g. 30%. To the mixture is added an equal amount of ethyl acetate to extract AX-2. To the AX-2 containing solution a small amount of ammonium sulfate is added with stirring. Ammonium sulfate is then removed from the solution, and the resultant supernatant is concentrated in vacuo. After removal of impurities by filtration, the solution is filtered and the filtrate is added to peteroleum ether to from a precipitate which is separated and dried in vacuo. The dried powder is dissolved in chloroform and passed through a column packed with silica gel filled with chloroform. The elution is effected by using a solvent system of chloroform/methanol (100:2 v/v). The chromatographed fractions containing AX-2 are collected, combined and concentrated in vacuo. The concentrated solution is added to petroleum ether to form a precipitate which is collected, combined and dried in vacuo. The powders are dissolved in ethyl acetate and transferred to a column packed with silica gel filled with ethyl acetate. The elution is effected by using a solvent system of ethyl acetate/acetone (100:5 v/v). The chromatographed fractions containing AX-2 are collected, combined and concentrated in vacuo. The concentrated solution is added to petroleum ether to form a precipiate which, after removal of the supernatant, is dried at room temperature in vacuo to obtain AX-2. In this case, the extraction of the active substance is effected at a pH of below 5.0, for example, from 3.0-5.0.

The acute toxicity and anti-tumour activity of AX-2 are as follows. I. Acute toxicity ($LD_{50}$) of AX-2:

Mice (ddy strain; male; weight 20±2 g; each group consisting of 5 mice) were used as test animals. On each occasion, the active substance of this invention was once administered to the animal by injection (ip. or iv.). For 14 days after administration, mice were observed to investigate the death ratio of each group, from which the acute toxicity was calculated by Behrens-Körber's method. $LD_{50}$ was 27 mg/kg (iv.) or 7.8 mg/kg (ip.).

II. Anti-tumour activity of AX-2:

(1) Effect on Sarcoma 180 solid tumour:

On each occasion, $5 \times 10^6$ cells of Sarcoma 180 solid tumour were implanted into the abdominal cavity of a ddy male mouse. 7 days after this, the cells were collected from the ascites. The cells were washed once with a sterilized physiological solution of sodium chloride and suspended in a sterilized physiological solution of sodium chloride at a concentration of $5 \times 10^7$ cells/ml, of which 0.1 ml was implanted under the skin at the right artpit of a ddy male mouse having a weight of 20±2 g. 24 hours after this, the active substance was administered into the vein at the tail of each mouse of a group consisting of 5 mice. In order to investigate the anti-tumour activity, 7 days after administration of AX-2, the major axis (a) and minor axis (b) of the tumour were measured, from which the volume of the tumour was calculated as a $\times b^2/2$. The effect of AX-2 is expressed by T/C which denotes the volume ratio of T [mice administered with AX-2] to C (untreated group). Table 1 indicates the effect of AX-2 agsinst Sarcoma 180 solid tumour by injection (iv.).

TABLE 1

| Compound | Dose (mg/kg) | T/C | Survials (7 days) | Peripherical leucocytes count (WBC) ± SD/mm$^3$ | $ED_{50}$ (mg/kg) |
| --- | --- | --- | --- | --- | --- |
| AX-2 | 1.88 | 0.77 | 4/4 | 7730 ± 49 | |
| | 3.75 | 0.64 | 4/4 | 6730 ± 115 | |
| | 7.5 | 0.42 | 4/4 | 4100 ± 55 | 5.7 |
| | 10 | 0.34 | 4/4 | 2800 ± 80 | |
| | 15 | 0.25 | 4/4 | 2950 ± 42 | |
| | 30 | 0.05 | 3/4 | 2300 ± 60 | |

By administering AX-2 at a dose of 7.5 to 15 mg/kg, the effect increased according to the increased dose. A T/C of 0.25 was obtained from the group, to which each 15 mg/kg of AX-2 had been administered. In this table, $ED_{50}$ denotes a dose capable of reducing the volume of the tumour to 50% of the corresponding volume of the control group. Such volumes were calculated by plotting a relation between the dose and T/C on a logarithmic graph which indiates T/C on the ordinate and the dose on the abscissa, and calculating the dose and anti-tumour activity as a straight line by the method of least squares. The dose corresponding to T/C of 0.5 is defined as $ED_{50}$.

The peripherical leucocytes count (WBC) was measured by using a micro cell counter in the following manner. Sarcoma 180 solid tumour was implanted by injection (ip.). 4 days after this, blood was collected from the eye ground, of which 20 μl was added to 9.98 ml of Cellkit-7 (a reagent commercially available from Toyo Rika K.K., Japan) to dissolve the red cells. In this solution a drop of saponin was dispersed, followed by measuring with a micro cell counter.

(2) Effects on Melanoma $B_{16}$ tumour:

Tumour cells were collected from Melanoma $B_{16}$ tumour cells lined in the abdominal cavity of a $C_{57}BL/6$ male mouse and suspended in a sterilized physiological solution of sodium chloride at a concentration of $2.5 \times 10^7$ cell/ml, of which 0.2 ml was implanted into the abdominal cavity of each mouse. The anti-tumour activity was indicated by T/C % where T and C respectively indicate the average survival days of treated and untreated groups. Table 2 shows the effects of AX-2 upon Melanoma $B_{14}$ by injection (ip.)

TABLE 2

| Compound | Dose (mg/kg) | Average survival days (days ± SD) | T/C | Survived after 60 days after implantation |
|---|---|---|---|---|
| — | | 12.8 ± 1.1 | | |
| AX-2 | 0.031 | 18.4 ± 1.5 | 144 | 0/5 |
| | 0.063 | 13.0 ± 1.7 | 140 | 0/5 |
| | 0.125 | 19.4 ± 2.0 | 152 | 0/5 |
| | 0.25 | 17.8 ± 1.1 | 140 | 0/5 |
| | 0.5 | 21.0 ± 2.8 | 164 | 0/5 |
| | 1.0 | 24.0 ± 3.5 | 189 | 0/5 |
| | 2.0 | 27.4 ± 5.4 | 214 | 0/5 |
| | 4.0 | 33.4 ± 9.2 | 261 | 0/5 |
| | 6.0 | 35.4 ± 5.3 | >277 | 1/5 |
| | 8.0 | 10.6 ± 4.2 | 93 | 0/5 |
| | 12.0 | 4.8 ± 1.6 | 26 | 0/5 |

As apparent from this table, it was noted that by administration of AX-2 in an amount of 6 mg/kg, the T/C value was more than 277% and 1/5 of the mice were alive 60 days after the beginning of the administration. The therapeutic index [a dose showing a maximum therapeutic effect/a dose showing a T/C of 130%] was 193.

The present invention further provides an antitumour composition comprising as actvie ingredient an effective amount of AX-2 as hereinbefore defined in association with a pharmaceutically acceptable carrier or excipient.

AX-2 may be used, for example, in the form of an injecting agent which may take a dosage unit form well known in the art. For example, AX-2 may be dissolved in a small amount of ethanol, which may further be dissolved for example in a physiological solution of sodium chloride, injecting solution of glucose, fructose, mannitol and the like for used for intravenous injection. In such a case, AX-2 may be freeze-dried before use for preservation according to the Pharmacepoeia of Japan, although it is possible, if desired, to prepare an injection powder by using sodium chloride. For oral administration, a suitable excipient may be used to prepare, for example, tablets, powders, granules and the like in conventional manner. If desired, AX-2 may be administered into the artery, abdominal cavity and thoracic cavity. The dose of AX-2 may vary, depending upon various factors such as, for example, the age of patient, symptom and the like. For example, it is preferred to administer AX-2 in an amount of 1 to 50 mg per adult human.

The following non-limiting examples illustrate the invention.

EXAMPLE 1

*Streptomyces caespitosus* T-17-135 (NRRL 12508) was used as seed which was inoculated to a seed medium [300 ml in a 2 l Erlenmeyer flask; composed of glucose (1 g/dl), yeast (1 g/dl), starch (0.5 g/dl), sodium chloride (0.5 g/dl) and calcium carbonate (0.3 g/dl); pH=7.2] for culturing at 28° C. for 3 days. The resultant seed medium (1.5 l) was added to a second medium (100 l) similar to the first medium for culturing at 28° C. for 3 days with aeration. The thus-obtained medium was added to a main medium (1 kl) composed of fructose (2 g/dl), soybean meal (4 g/dl), starch (1 g/dl), sodium chloride (0.5 g/dl) and calcium carbonate (0.5 g/dl) and having a pH of 7.2 for culturing at 30° C. for 2 days. N-propanol (80 l) and Radiolite #500 (60 kg; commercial product of Showa Kagaku Kogyo K.K., Japan) were added to the resultant cultured broth, from which the cells were removed by using a filter press. The filtrate was charged to a column packed with Diaion HP-20 (50 l; commercial product of Mitsubishi Kasei Kogyo K.K., Japan) to adsorb the active material. The resin was washed with water and was then treated with a 40 % aqueous solution of methanol (150 l) to remove impurities, followed by elution with a 80% aqueous solution of methanol (150 l) to give a fraction containing AX-2. After concentrating in vacuo, the solution was adjusted to a pH of 4.5 with diluted sulfuric acid. To this solution ethyl acetate was added to extract AX-2. The ethyl acetate layer containing AX-2 was fractionated and added with anhydrous sodium sulfate. The mixture was well stirred and anhydrous sodium sulfate was removed. The flitrate was concentrated in vacuo to 100 ml and was transferred to a column packed with silica gel (3 l, filled with ethyl acetate; commercial product of Kanto Kagaku K.K., Japan) having 100–200 meshes. The elution was effected by using a solvent system of ethyl acetate/acetone (100:5 v/v). AX-2 containing fractions resulted from the chromatographic treatment were collected and combined, and the combined fractions were added to petroleum ether to give precipitates. The precipitates were separated and dried at room temperature in vacuo to obtain AX-2 substance (258 mg).

EXAMPLE 2

Pharmaceutical Composition Containing AX-2

Under sterilized conditions, powder of AX-2 substance (10 mg) is poured into a sterilized brown vial ( capacity of 10 ml). In use, a sterilized 50% aqueous ethanol solution (5 ml) is added to the vial and well stirred to prepare an injectiong solution.

We claim:

1. A substance represented by the formula:

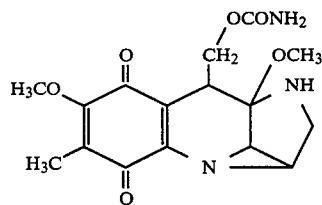

2. An anti-tumour composition comprising as active ingredient an anti-tumour effective amount of a substance of claim 1 in combination with a pharmaceutically acceptable carrier.

3. The composition of claim 2 wherein the active ingredient is present in 1 to 50 mg per adult human dosage.

4. The composition of claim 1 wherein said carrier is ethenol.

* * * * *